United States Patent
Chen et al.

(10) Patent No.: US 11,395,791 B2
(45) Date of Patent: Jul. 26, 2022

(54) METHODS OF INDUCING SIGA AND MUCIN 5B IN THE ORAL CAVITY

(71) Applicant: Colgate-Palmolive Company, New York, NY (US)

(72) Inventors: Dandan Chen, Bridgewater, NJ (US); Harsh Mahendra Trivedi, Hillsborough, NJ (US); Ying Yang, Monmouth Junction, NJ (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/717,821

(22) Filed: Dec. 17, 2019

(65) Prior Publication Data

US 2020/0206106 A1 Jul. 2, 2020

Related U.S. Application Data

(60) Provisional application No. 62/785,161, filed on Dec. 26, 2018.

(51) Int. Cl.

| | |
|---|---|
| A61K 8/24 | (2006.01) |
| A61K 8/21 | (2006.01) |
| A61K 8/25 | (2006.01) |
| A61K 8/04 | (2006.01) |
| A61K 8/02 | (2006.01) |
| A61K 8/365 | (2006.01) |
| A61Q 11/00 | (2006.01) |
| A61K 8/27 | (2006.01) |

(52) U.S. Cl.
CPC .............. A61K 8/24 (2013.01); A61K 8/022 (2013.01); A61K 8/0254 (2013.01); A61K 8/042 (2013.01); A61K 8/21 (2013.01); A61K 8/25 (2013.01); A61K 8/27 (2013.01); A61K 8/365 (2013.01); A61Q 11/00 (2013.01); *A61K 2800/28* (2013.01); *A61K 2800/92* (2013.01)

(58) Field of Classification Search
CPC .................................................. A61Q 11/00
See application file for complete search history.

(56) References Cited

U.S. PATENT DOCUMENTS

| | | | |
|---|---|---|---|
| 6,221,340 B1 * | 4/2001 | Yu | A61K 8/22 424/49 |
| 10,258,551 B2 | 4/2019 | Rege | |
| 10,278,906 B2 | 5/2019 | Rege | |
| 10,285,929 B1 | 5/2019 | Bretz | |
| 2012/0207686 A1 * | 8/2012 | Fruge | A61P 31/04 424/52 |
| 2017/0367949 A1 * | 12/2017 | Rege | A61Q 11/00 |
| 2019/0192394 A1 | 6/2019 | Rege | |
| 2019/0192395 A1 | 6/2019 | Rege | |

FOREIGN PATENT DOCUMENTS

| | | |
|---|---|---|
| WO | 2017/223292 | 12/2017 |
| WO | 2017/223311 | 12/2017 |

OTHER PUBLICATIONS

Google patent search pH for stannous fluoride buffer_Jul. 2, 2020 (Year: 2020).*
"Buffers" from the University of California at Berkeley (downloaded Jul. 2, 2020 from http://microscopy.berkeley.edu/Resources/instruction/buffers.html; available on the internet Oct. 12, 2004) (Year: 2004).*
Siga levels and toothbrushing—Google Scholar (Year: 2021).*
Daniel J. Smith and Martin A. Taubman. Effect of Local Deposition of Antigen on Salivary Immune Responses and Reaccumulation of Mutans *Streptococci*. Journal of Clinical Immunology, vol. 10, No. 5, 1990. (Year: 1990).*
WebMD. When and how long should you brush your teeth. Downloaded Feb. 4, 2021 from https://web.archive.org/web/20160708162530/https://www.mayoclinic.org/healthy-lifestyle/adult-health/expert-answers/brushing-your-teeth/faq-20058193; dated Jul. 8, 2016. (Year: 2016).*
A. Gornowicz et al. "The assessment of sIgA, histatin-5, and lactoperoxidase levels in saliva of adolescents with dental caries," Med Sci Monit, 2014; 20: 1095-1100. (Year: 2014).*
P. Brandtzaeg. "Do Salivary Antibodies Reliably Reflect Both Mucosal and Systemic Immunity?," Ann. N.Y. Acad. Sci. 1098: 288-311 (2007). (Year: 2007).*
Marite Cardenas, Ulla Elofsson, and Liselott Lindh. "Salivary Mucin MUC5B Could Be an Important Component of in Vitro Pellicles of Human Saliva: An in Situ Ellipsometry and Atomic Force Microscopy Study," Biomacromolecules 2007, 8, 1149-1156. (Year: 2007).*
Google_scholar_search_8-28-2021_sIgA_levels_plasma_cells-in_salivary_glands_dental_caries (Year: 2021).*
Google_scholar_search_8-28-2021_mucin_5B_and_slgAoraLcavity (Year: 2021).*
Ployon et al., 2016, "The membrane-associated MUC1 improves adhesion of salivary MUC5B on buccal cells. Application to development of an in vitro cellular model of oral epithelium," Archives of Oral Biology 61:149-155.
Algarni et al., 2015, "The impact of Stannous, Flouride ions and its combination on Enamel Pellicle Proteome and Dental Erosion Prevention," Plos One 10(6):6-8.

(Continued)

*Primary Examiner* — Michael P Cohen

(57) ABSTRACT

Methods of increasing sIgA and mucin 5B levels in an individual's oral cavity are disclosed. The methods comprise applying to the individual's oral cavity in an amount effective to increase sIgA and mucin 5B levels in the individual's oral cavity, an oral care composition comprising: zinc phosphate, stannous fluoride and optionally, an organic acid buffer system.

26 Claims, 9 Drawing Sheets

(56) References Cited

OTHER PUBLICATIONS

International Search Report and the Written Opinion of the International Searching Authority issued in International Application PCT/US2019/066926 dated Apr. 9, 2020.
Kheirouri et al., 2014, "Decreased serum and mucosa immunoglobulin A levels in vitamin A- and zinc-deficient mice," Central European Journal of Immunology 2:165-169.

* cited by examiner

METHODS OF INDUCING SIGA AND MUCIN 5B IN THE ORAL CAVITY

BACKGROUND

Mucus forms a protective coating on wet epithelial surfaces throughout the body that houses the microbiota and plays a key role in host defense. Mucins, the primary structural components of mucus that creates its viscoelastic properties, are critical components of the gel layer that protect against invading pathogens. Different types of mucins exist throughout the body in various locations such as the oral cavity.

Mucins may play a role in cell signal transduction and could form scaffolds for secreted mucins to bind. Each of the salivary mucins MUC5B, MUC7, MUC19, MUC1, and MUC4 are composed of a unique domain structure that influences the mucins' physical properties and localization in the oral cavity. MUC5B is the primary gel-forming mucin in the mouth that is secreted by mucous cells in the submandibular, sublingual, palatine, and labial salivary glands MUC5B have several aspects of its primary sequences that determine its ability to form gels and higher order structures. MUC5B is composed of a protein backbone with glycan chains radiating outward to form a 'bottle-brush' structure. The MUC5B backbone is composed of approximately 5,700 amino acids and is broadly organized into the N-terminus, central glycosylated region, and C-terminus. MUC5B's central glycosylated region contains repeating units of 29 amino acids that are rich in serine and threonine. The C-terminal domain participates in disulfide bond formation, which links individual MUC5B monomers into dimers, and then polymer chains form through disulfide bond formation at the N-terminus.

MUC5B protects the oral cavity by binding to antibacterial salivary proteins, which can influence the proteins' localization in the oral cavity, increase their retention time, and alter their biological activity. In some cases, salivary mucins have been shown to be involved in sIgA binding to the mucosal pellicle, which would enhance sIgA concentration near the oral epithelium. MUC5B binding to this select group of salivary proteins indicates that the formation of these complexes is protein specific. Salivary mucins may serve as carriers for antibacterial salivary proteins to transport them throughout the oral cavity, increase their retention in the dental pellicle, and/or protect proteins from proteolytic degradation through the formation of complexes. MUC5B's ability to form a gel layer that guards against pathogenic microbes but does not cause bacterial killing is a unique property that contrasts with other defense proteins in saliva, such as antimicrobial peptides.

Secretory Immunoglobulin A (SIgA) is a subclass of Immunoglobulin A (IgA), an antibody that plays a critical role in mucosal immunity. SIgA is the main immunoglobulin found in mucous secretions from, inter alia, salivary glands. SIgA is not synthesized by mucosal epithelial cells but instead, it is produced by B-lymphocytes adjacent to the mucosal cells, then transported through the cell interiors, and released into the secretions from the cells. SIgA plays a key role in protecting vulnerable areas such as the oral cavity from invading pathogens.

BRIEF SUMMARY

Methods of protecting an individual against pathogenic oral bacteria are provided.

Methods of increasing sIgA and mucin 5B levels in an individual's oral cavity are provided. The methods comprise applying to the individual's oral cavity in an amount effective to increase sIgA and mucin 5B levels in the individual's oral cavity, an oral care composition comprising: zinc phosphate, stannous fluoride and optionally, an organic acid buffer system.

DETAILED DESCRIPTION

Figure 1:
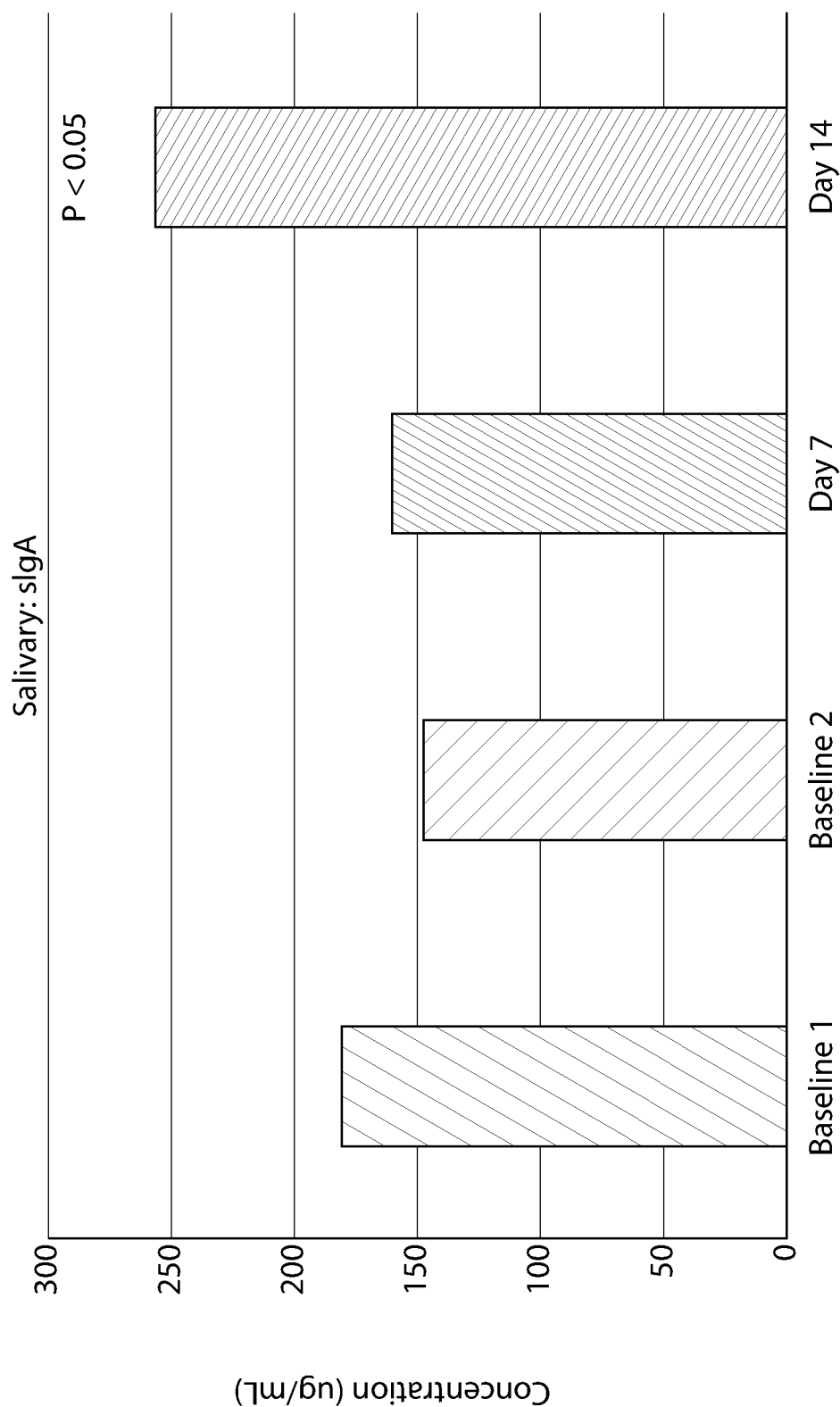
FIG. 1 shows data from ELISA assays of saliva samples tested for sIgA.

Application of oral care compositions to the oral cavity of an individual can promote increased levels of sIgA and mucin 5B in the oral cavity. These proteins protect the individual from pathogenic microbes and it is therefore desirable to increase the level of these proteins in the oral cavity.

Mucin 5B and sIgA levels are increased in the oral cavity by applying an oral care composition to the oral cavity in an amount effect to promote increased levels of mucin 5B and sIgA. Oral care compositions comprise an orally acceptable carrier, zinc phosphate and stannous fluoride. In further embodiments, oral care composition further comprises and an organic acid buffer system.

Toothpastes and oral gels may comprise from 1.0% to 99% water, by weight of the composition. For example, the composition may comprise at least 10%, 15%, 20%, 25%, 30%, 35% or 40% water, up to a maximum of, for example, 60%, 70%, 80%, 90%, 95% or 99% water, by weight of the composition. As used herein, amounts of water refer to water added directly to the composition, as well as water added as part of ingredients or components which are added as aqueous solutions. In some embodiments, the composition comprises 10-60% water, or 10-50% water, or 10-40% water, or 10-30% water, or 15-30% water, or 20-30% water, or about 25% water, by weight of the composition, "Preformed salt" when used in reference to zinc phosphate means that the zinc phosphate is not formed in situ in the oral care composition, e.g., through the reaction of phosphoric acid and another zinc salt.

In some embodiments, the zinc phosphate is a preformed salt of zinc phosphate. The zinc phosphate is present in an amount sufficient so that the stannous fluoride dissociates to provide a therapeutically effective amount of stannous ions in aqueous solution. The amount of zinc phosphate is preferably from 0.05 to 10% by weight relative to the weight of the oral care composition, preferably from 0.05 to 5% by weight, relative to the weight of the oral care composition, for example, for example, from 0.1 to 8% by weight or from 0.1 to 4% by weight, or from 0.5 to 5% by weight, or from 0.5 to 4% by weight, or from 0.5 to 3% by weight, or from 0.5 to 2% by weight, or from 0.8 to 1.5% by weight, or from 0.9 to 1.1% by weight, or about 1% by weight, or from 1 to 4%, or from 1 to 3% by weight, or from 2 to 3% by weight, or about 2%, or about 2.25% or about 2.5%, by weight.

The amount of the stannous fluoride is preferably from 0.01% to 11% by weight from 0.01% to 5% by weight, relative to the weight of the oral care composition, for example, from 0.05 to 4% by weight, or from 0.1% to 3% by weight, from 0.05% to 11% by weight, relative to the weight of the oral care composition, for example, from 0.05 to 7% by weight, or from 0.1% to 5% by weight, or from 0.2 to 3% by weight, or from 0.2 to 2% by weight, or from 0.2 to 1% by weight, or from 0.2 to 0.8% by weight, or from 0.3 to 1% by weight, or from 0.4 to 0.8% by weight, or from 0.4 to 0.6% by weight, or from 0.4 to 0.5% by weight, or about 0.45%> by weight (e.g., 0.454%).

In some embodiments, the amount of the water is 10% by weight or more, or about 12% by weight or more, relative to the weight of the oral care composition, for example, 10-90%, or 10-80%, or 10-70%, or 10-60%, or 10-50%, or 10-40%, or 10-30%, or from 15% to 85%, or 15-30%, or from 20% to 75%, or from 20-50% or from 20% to 40% or from 20% to 30%, or from 25% to 50%, or from 30% to 40%, or 30-35%, for example, about 35%, or about 30%, or about 25% or about 20%.

The optional organic buffer system may comprise a carboxylic acid and one or more conjugate base salts thereof, for example, alkali metal salts thereof (e.g., citric acid and sodium citrate). An acid may be selected from citric acid, lactic acid, malic acid, maleic acid, fumaric acid, acetic acid, succinic acid, and tartaric acid. One or more conjugate base salts may be independently selected from sodium and potassium salts, or combinations thereof. Some embodiments optionally comprise citric acid, and the one or more conjugate base salts comprise monosodium citrate (monobasic), disodium citrate (dibasic), tri sodium citrate (tribasic), and combinations thereof. In some embodiments, the optional organic acid buffer system is present in an amount of 0.1 to 5.0% by weight of the composition, measured as the combined amount of organic acid and any conjugate base salts; for example, from 0.5 to 4.0%, or from 1.0 to 3.0%, or from 1.5 to 3.0%, or from 1.0 to 2.4%, or from 1.0% to 2.0%, or from 1.0% to 1.5%, or about 1.2%, by weight of the composition. In some embodiments, the optional organic acid buffer system consists of an organic acid and a conjugate base salt thereof, for example, in a ratio of from 1:1 to 1:10, e.g., from 1:2 to 1:8, or from 1:3 to 1:6, or from 1:4 to 1:6, or from 1:5 to 1:6, or about 1:5, by weight of the components. In some embodiments, the optional organic acid buffer system comprises citric acid and a sodium citrate salt (e.g., trisodium citrate, disodium citrate, or monosodium citrate), in a ratio of from 1:3 to 1:6, or 1:4 to 1:6, or about 1:5 (e.g., about 1:5.7), by weight.

In some embodiments, the oral care composition further comprises an abrasive, for example, silica abrasives, calcium abrasives, and other abrasives as disclosed herein, and/or one or more humectants and/or one or more surfactants, as described herein and/or an effective amount of one or more alkali phosphate salts for example orthophosphates, pyrophosphates, tripolyphosphates, tetraphosphates or higher polyphosphates. In some embodiments, the alkali phosphate salts comprise tetrasodium pyrophosphate or tetrapotassium pyrophosphate, for example, in an amount of 0.5 to 5% by weight of the composition, e.g., 1-3%, or 1-2% or about 2%> by weight, or about 2-4%, or about 3-4% or about 4% by weight of the composition. In some embodiments, the alkali phosphate salts comprise sodium tripolyphosphate or potassium tripolyphosphate, for example, in an amount of 0.5 to 6% by weight of the composition, e.g., 1-4%, or about 2~3%> or about 3%> by weight. Any preceding composition, further comprising a whitening agent and/or one or more sources of zinc ions in addition to the zinc phosphate, for example a zinc salt selected from zinc citrate, zinc oxide, zinc lactate, zinc pyrophosphate, zinc sulfate, or zinc chloride. In some embodiments, such compositions are dentifrices (e.g., a toothpaste or oral gel), powder (e.g., tooth powder), lozenge, mint, cream, strip or gum (e.g., chewing gum).

In some embodiments, the composition comprises from 0.5 to 3% by weight zinc phosphate; from 0.05 to 11% by weight stannous fluoride; from 1 to 8% by weight alkali phosphate salts selected from sodium phosphate dibasic, potassium phosphate dibasic, dicalcium phosphate dihydrate, tetrasodium pyrophosphate, tetrapotassium pyrophosphate, calcium pyrophosphate, sodium tripolyphosphate, and mixtures of any two or more of these, relative to the weight of the oral care composition, and a silica abrasive. The composition may be essentially free of a halogenated diphenyl ether. The composition may be a single-phase composition or a dual-phase composition. The composition may be free of one or more of zinc oxide, zinc citrate, or zinc lactate. Zinc phosphate may the only zinc ion source. The composition may be essentially free of hexametaphosphate salts (e.g., sodium hexametaphosphate).

Formulations can include stannous levels, provided by stannous fluoride, ranging for example, from 3,000 ppm to 15,000 ppm (mass fraction) stannous ions in the total composition. In embodiments, the soluble stannous content can range from 0.1 wt % to 0.5 wt %, or more, such as from 0.15 wt % to 0.32 wt %, based on the total weight of the composition.

The compositions may optionally comprise additional ingredients suitable for use in oral care compositions. Examples of such ingredients include active agents, such as a fluoride source and/or a phosphate source in addition to zinc phosphate. The compositions may be formulated in a suitable dentifrice base, e.g., comprising abrasives, e.g., silica abrasives, surfactants, foaming agents, vitamins, polymers, enzymes, humectants, thickeners, additional antimicrobial agents, preservatives, flavorings, colorings, and/or combinations thereof. Examples of suitable dentifrice bases are known in the art. Alternatively, the compositions may be formulated as a gel (e.g., for use in a tray), chewing gum, lozenge or mint. Examples of suitable additional ingredients that can be employed in the compositions of the present disclosure are discussed in more detail below.

Oral care compositions comprise arginine or a salt thereof. In some embodiments, the arginine is L-arginine or a salt thereof. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion. In some embodiments, the arginine in partially or wholly in salt form such as arginine phosphate, arginine hydrochloride or arginine bicarbonate. In some embodiments, the arginine is present in an amount corresponding to 0.1% to 15%, e.g., 0.1 wt % to 10 wt %, e.g., 0.1 to 5 wt %, e.g., 0.5 wt % to 3 wt % of the total composition weight, about e.g., 1%, 1.5%, 2%, 3%, 4%, 5%, or 8%, wherein the weight of the arginine is calculated as free form. In some embodiments the arginine is present in an amount corresponding to about 0.5 wt. % to about 20 wt. % of the total composition weight, about 0.5 wt. % to about 10 wt. % of the total composition weight, for example about 1.5 wt. %, about 3.75 wt. %, about 5 wt. %, or about 7.5 wt. % wherein the weight of the arginine is calculated as free form. In some embodiments, the arginine is present in an amount of from 0.5 weight % to 10 weight %, or from 0.5 weight % to 3 weight % or from 1 weight % to 2.85 weight %, or from 1.17 weight % to 2.25 weight %, based or from 1.4 weight % to 1.6 weight %, or from 0.75 weight % to 2.9 weight %, or from 1.3 weight % to 2 weight %, or about 1.5 weight %, based on the total weight of the composition. Typically, the arginine is present in an amount of up to 5% by weight, further optionally from 0.5 to 5% by weight, still further optionally from 2.5 to 4.5% by weight, based on the total weight of the oral care composition. In some embodiments, arginine is present in an amount from 0.1 wt. %-6.0 wt. %. (e.g., about 1.5 wt %) or from about 4.5 wt. %-8.5 wt. % (e.g., 5.0%) or from 3.5 wt. %-9 wt. % or 8.0 wt. %. In some embodiments, the arginine is present in a dentifrice, at for example about 0.5-2 wt. %, e.g., and about 1% in the case of a mouthwash.

One or more fluoride ion sources are optionally present in an amount providing a clinically efficacious amount of soluble fluoride ion to the oral care composition. A fluoride ion source is useful, for example, as an anti-caries agent. Any orally acceptable particulated fluoride ion source can be used, including stannous fluoride, sodium fluoride, potassium fluoride, potassium monofluorophosphate, sodium monofluorophosphate, ammonium monofluorophosphate, sodium fluorosilicate, ammonium fluorosilicate, indium fluoride, amine fluoride such as olaflur (N'-octadecyltrimethylendiamine-N,N,N'-tris(2-ethanol)-dihydrofluoride), ammonium fluoride, titanium fluoride, hexafluorosulfate, and combinations thereof. Fluoride where present may be present at levels of, e.g., about 25 to about 25,000 ppm, for example about 50 to about 5000 ppm, about 750 to about 2,000 ppm for a consumer toothpaste (e.g., 1000-1500 ppm, e.g., about 1000 ppm, e.g., about 1450 ppm), product. In some embodiments, fluoride is present from about 100 to about 1000, from about 200 to about 500, or about 250 ppm fluoride ion. 500 to 3000 ppm. In some embodiments, the fluoride source provides fluoride ion in an amount of from 50 to 25,000 ppm (e.g., 750-7000 ppm, e.g., 1000-5500 ppm, e.g., about 500 ppm, 1000 ppm, 1100 ppm, 2800 ppm, 5000 ppm, or 25000 ppm). In some embodiments, the fluoride source is stannous fluoride. In some embodiments, the fluoride source is stannous fluoride which provides fluoride in an amount from 750-7000 ppm (e.g., about 1000 ppm, 1100 ppm, 2800 ppm, 5000 ppm). In some embodiments, the fluoride source is stannous fluoride which provides fluoride in an amount of about 5000 ppm. In some embodiments, the fluoride source is sodium fluoride which provides fluoride in an amount from 750-2000 ppm (e.g., about 1450 ppm). In some embodiments, the fluoride source is selected from sodium fluoride and sodium monofluorophosphate and which provides fluoride in an amount from 1000 ppm-1500 ppm. In some embodiments, the fluoride source is sodium fluoride or sodium monofluorophosphate and which provides fluoride in an amount of about 1450 ppm. In some embodiments, stannous fluoride is the only fluoride source. In some embodiments, the fluoride source is stannous fluoride which provides fluoride in an amount from 750-7000 ppm (e.g., about 1000 ppm, 1100 ppm, 2800 ppm, 5000 ppm). In some embodiments, the fluoride source is stannous fluoride which provides fluoride in an amount of about 5000 ppm. Fluoride ion sources may be added to the compositions at a level of about 0.001 wt. % to about 10 wt. %, e.g., from about 0.003 wt. % to about 5 wt. %, 0.01 wt. % to about 1 wt., or about 0.05 wt. %. In some embodiment, the stannous fluoride is present in an amount of 0.1 wt. % to 2 wt. % (0.1 wt %-0.6 wt. %) of the total composition weight. Fluoride ion sources may be added to the compositions at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. In some embodiment, the fluoride source is a fluoride salt present in an amount of 0.1 wt. % to 2 wt. % (0.1 wt %-0.6 wt. %) of the total composition weight (e.g., sodium fluoride (e.g., about 0.32 wt. %) or sodium monofluorophosphate). e.g., 0.3-0.4%, e.g., ca. 0.32% sodium fluoride The oral care compositions described herein may also comprise one or more further agents such as those typically selected from the group consisting of: abrasives, an antiplaque agent, a whitening agent, antibacterial agent, cleaning agent, a flavoring agent, a sweetening agent, adhesion agents, surfactants, foam modulators, pH modifying agents, humectants, mouth-feel agents, colorants, tartar control (anti-calculus) agent, polymers, saliva stimulating agent, nutrient, viscosity modifier, anti-sensitivity agent, antioxidant, and combinations thereof.

In some embodiments, the oral care compositions comprise one or more abrasive particulates such as those useful for example as a polishing agent. Any orally acceptable abrasive can be used, but type, fineness, (particle size) and amount of abrasive should be selected so that tooth enamel is not excessively abraded in normal use of the composition. Examples of abrasive particulates may be used include abrasives such sodium bicarbonate, insoluble phosphates (such as orthophosphates, polymetaphosphates and pyrophosphates including dicalcium orthophosphate dihydrate, calcium pyrophosphate, tricalcium phosphate, calcium polymetaphosphate and insoluble sodium polymetaphosphate), calcium phosphate (e.g., dicalcium phosphate dihydrate), calcium sulfate, natural calcium carbonate (CC), precipitated calcium carbonate (PCC), silica (e.g., hydrated silica or silica gels or in the form of precipitated silica or as admixed with alumina), iron oxide, aluminium oxide, aluminum silicate, calcined alumina, bentonite, other siliceous materials, perlite, plastic particles, e.g., polyethylene, and combinations thereof. The natural calcium carbonate abrasive of is typically a finely ground limestone which may optionally be refined or partially refined to remove impurities. The material preferably has an average particle size of less than 10 microns, e.g., 3-7 microns, e.g. about 5.5 microns. For example, a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004%) by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8-4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use include, for example, Carbolag® 15 Plus from Lagos Industria Quimica. In some embodiments, additional calcium-containing abrasives, for example calcium phosphate abrasive, e.g., tricalcium phosphate, hydroxyapatite or dicalcium phosphate dihydrate or calcium pyrophosphate, and/or silica abrasives, sodium metaphosphate, potassium metaphosphate, aluminum silicate, calcined alumina, bentonite or other siliceous materials, or combinations thereof are used. Examples of silica abrasives include, but are not limited to, precipitated or hydrated silicas having a mean particle size of up to about 20 microns (such as Zeodent 105 and Zeodent 1 14 marketed by J. M. Huber Chemicals Division, Havre de Grace, Md. 21078); Sylodent 783 (marketed by Davison Chemical Division of W.R. Grace & Company); or Sorbosil AC 43 (from PQ Corporation). In some embodiments, an effective amount of a silica abrasive is about 10-30%, e.g. about 20%. In some embodiments, the acidic silica abrasive Sylodent is included at a concentration of about 2 to about 35% by weight; about 3 to about 20% by weight, about 3 to about 15% by weight, about 10 to about 15% by weight. For example, the acidic silica abrasive may be present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %. Sylodent 783 has a pH of 3.4-4.2 when measured as a 5% by weight slurry in water and silica material has an average particle size of less than 10 microns, e.g., 3-7 microns, e.g. about 5.5 microns. In some embodiments, the silica is synthetic amorphous silica, (e.g., 1%-28% by wt.) (e.g., 8%-25% by wt). In some embodiments, the silica abrasives are silica gels or precipitated amorphous silicas, e.g. silicas having an average particle size ranging from 2.5 microns to 12 microns. Some embodiments further comprise a small particle silica having a median particle size (d50) of 1-5 microns (e.g., 3-4 microns) (e.g., about 5 wt. % Sorbosil AC43 from PQ Corporation Warrington, United Kingdom). The composition may contain from 5 to 20 wt % small particle silica, or for example 10-15 wt %, or for example 5 wt %, 10 wt %, 15 wt % or 20 wt % small particle silica. In some embodiments, 20-30 wt % of the total silica in the composition is small particle silica (e.g., having a median particle size (d50) of 3-4 microns and wherein the small particle silica is about 5 wt. % of the oral care composition. In some embodiments, silica is used as a thickening agent, e.g., particle silica. In some embodiments, the composition comprises calcium carbonate, such as precipitated calcium carbonate high absorption (e.g., 20% to 30% by weight of the composition or, 25% precipitated calcium carbonate high absorption), or precipitated calcium carbonate—light (e.g., about 10% precipitated calcium carbonate—light) or about 10% natural calcium carbonate.

In some embodiments, the oral care compositions comprise a whitening agent, e.g., a selected from the group consisting of peroxides, metal chlorites, perborates, percarbonates, peroxyacids, hypochlorites, hydroxyapatite, and combinations thereof. Oral care compositions may comprise hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example, calcium peroxyphosphate, sodium perborate, sodium carbonate peroxide, sodium peroxyphosphate, and potassium persulfate or hydrogen peroxide polymer complexes such as hydrogen peroxide-polyvinyl pyrrolidone polymer complexes.

In some embodiments, the oral care compositions comprise an effective amount of one or more antibacterial agents, for example comprising an antibacterial agent selected from halogenated diphenyl ether (e.g. triclosan), triclosan monophosphate, herbal extracts and essential oils (e.g., rosemary extract, tea extract, magnolia extract, thymol, menthol, eucalyptol, geraniol, carvacrol, citral, hinokitol, magonol, ursolic acid, ursic acid, morn, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine furanones, bacteriocins, ethyllauroyl arginate, arginine bicarbonate, a Camellia extract, a flavonoid, a flavan, halogenated diphenyl ether, creatine, sanguinarine, povidone iodine, delmopinol, salifluor, metal ions (e.g., zinc salts, stannous salts, copper salts, iron salts), propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nisin preparations, chlorite salts; parabens such as methylparaben or propylparaben and mixtures of any of the foregoing. One or more additional antibacterial or preservative agents may optionally be present in the composition in a total amount of from about 0.01 wt. % to about 0.5 wt. %, optionally about 0.05 wt. % to about 0.1 wt. % or about 0.3%. by total weight of the composition.

In some embodiments, the oral care compositions may comprise at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of about 0.1 wt. % to about 50 wt. %, for example about 1 wt. % to 20 wt. %, by total weight of the composition.

In some embodiments, the oral care compositions also comprise at least one flavorant, useful for example to enhance taste of the composition. Any orally acceptable natural or synthetic flavorant can be used, including without limitation essential oils and various flavoring aldehydes, esters, alcohols, and similar materials, tea flavors, vanillin, sage, marjoram, parsley oil, spearmint oil, cinnamon oil, oil of wintergreen, peppermint oil, clove oil, bay oil, anise oil, eucalyptus oil, citrus oils, fruit oils, sassafras and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warning effects. Such ingredients illustratively include menthol, carvone, menthyl acetate, menthyl lactate, camphor, eucalyptus oil, eucalyptol, anethole, eugenol, cassia, oxanone, a-irisone, propenyl guaiethoi, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt. % to about 5 wt. %, for example, from about 0.03 wt. % to about 2.5 wt. %, optionally about 0.05 wt. % to about 1.5 wt. %, further optionally about 0.1 wt. % to about 0.3 wt. % and in some embodiments in various embodiments from about 0.01 wt. % to about 1 wt. %, from about 0.05 to about 2%, from about 0.1% to about 2.5%, and from about 0.1 to about 0.5% by total weight of the composition.

In some embodiments, the oral care compositions comprise at least one sweetener, useful for example to enhance taste of the composition. Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, ethanol, sorbitol, mannitol, xylitol, maltitol, isomalt, aspartame, neotame, saccharin and salts thereof (e.g. sodium saccharin), sucralose, dipeptide-based intense sweeteners, cyclamates, dihydrochalcones, glycerine, propylene glycol, polyethylene glycols, Poloxomer polymers such as POLOXOMER 407, PLURONIC F108, (both available from BASF Corporation), alkyl polyglycoside (APG), polysorbate, PEG40, castor oil, menthol, and mixtures thereof. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

In some embodiments, the oral care compositions further comprise an agent that interferes with or prevents bacterial attachment, e.g., ethyl lauroyl arginiate (ELA), solbrol or chitosan, as well as plaque dispersing agents such as enzymes (papain, glucoamylase, etc.).

In some embodiments, the oral care compositions also comprise at least one surfactant. Any orally acceptable surfactant, most of which are anionic, cationic, zwitterionic, nonionic or amphoteric, and mixtures thereof, can be used. Examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate, sodium coconut monoglyceride sulfonate, sodium lauryl sarcosinate, sodium lauryl isethionate, sodium laureth carboxylate and sodium dodecyl benzenesulfonate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of amides include N-lauryl sarcosine, and the sodium, potassium and ethanolamine salts of N-lauryl, N-myristoyl, or N-palmitoyl sarcosine. Examples of cationic surfactants include derivatives of aliphatic quaternary ammonium compounds having one long alkyl chain containing 8 to 18 carbon atoms such as lauryl trimethylammonium chloride, cetyl pyridinium chloride, cetyl trimethyl ammonium bromide, di-isobutylphenoxyethyldimethylbenzylammonium chloride, coconut alkyltrimethylammonium nitrite, cetyl pyridinium fluoride, and mixtures thereof. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, di alkyl sulfoxides and the like. Others include, for example, non-anionic polyoxyethylene surfactants, such as Polyoxamer 407, Steareth 30, Polysorbate 20, and castor oil; and amphoteric surfactants such as derivatives of aliphatic secondary and tertiary amines having an anionic group such as carboxylate, sulfate, sulfonate, phosphate or phosphonate such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly (ethylene oxide) with fatty acids, fatty, alcohols, fatty amides and other fatty moieties, and with propylene oxide and polypropylene oxides. In some embodiments, the oral composition includes a surfactant system that is sodium laurel sulfate (SLS) and cocamidopropyl betaine. One or more surfactants are optionally present in a total amount of about 0.01 wt. % to about 10 wt. %, for example, from about 0.05 wt. % to about 5 wt. %, or from about 0.1 wt. % to about 2 wt. %, e.g 1.5% wt. by total weight of the composition. In some embodiments, the oral composition include an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine. Some embodiments comprise a nonionic surfactant in an amount of from 0.5-5%, e.g, 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof. In some embodiments, the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407. Any of the preceding compositions may further comprise sorbitol, wherein the sorbitol is in a total amount of 10-40% (e.g., about 23%).

In some embodiments, the oral care compositions comprise at least, one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000, One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition In some embodiments, the oral care compositions comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates such as sodium bicarbonate, sesquicarbonates, borates, silicates, bisulfates, phosphates (e.g., monosodium phosphate, trisodium phosphate, monopotassium phosphate, dipotassium phosphate, tribasic sodium phosphate, sodium tripolyphosphate, phosphoric acid), imidazole, sodium phosphate buffer (e.g., sodium phosphate monobasic and disodium phosphate) citrates (e.g. citric acid, trisodium citrate dehydrate), pyrophosphates (sodium and potassium salts) and the like and combinations thereof. One or more pH modifying agents are optionally present in a total amount effective to maintain the composition in an orally acceptable pH range. Compositions may have a pH that is either acidic or basic, e.g., from pH 4 to pH 5.5 or from pH 8 to pH 10. In some embodiments, the amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%), in another embodiment about 15% to about 25%, by weight of the total composition.

In some embodiments, the oral care compositions also comprise at least one humectant. Any orally acceptable humectant can be used, including without limitation, polyhydric alcohols such as glycerin, sorbitol (optionally as a 70 wt. % solution in water), propylene glycol, xylitol or low molecular weight polyethylene glycols (PEGs) and mixtures thereof. Most humectants also function as sweeteners. In some embodiments, compositions comprise 15% to 70% or 30% to 65% by weight humectant. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein. One or more humectants are optionally present in a total amount of from about 1 wt. % to about 70 wt. %, for example, from about 1 wt. % to about 50 wt. %, from about 2 wt. % to about 25 wt. %, or from about 5 wt. % to about 15 wt. %, by total weight of the composition. In some embodiments, humectants, such as glycerin are present in an amount that is at least 20%>, e.g., 20-40%, e.g., 25-35%.

Mouth-feel agents include materials imparting a desirable texture or other feeling during use of the composition. In some embodiments, the oral care compositions comprise at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly i-carrageenan (iota-carrageenan), cellulosic polymers such as hydroxyethyl cellulose, and water-soluble salts of cellulose ethers (e.g., sodium carboxymethyl cellulose and sodium carboxymethyl hydroxyethyl cellulose), carboxymethylcellulose (CMC) and salts thereof, e.g., CMC sodium, natural gums such as karaya, xanthan, gum arabic and tragacanthin, colloidal magnesium aluminum silicate, colloidal silica, starch, polyvinyl pyrrolidone, hydroxyethyl propyl cellulose, hydroxybutyl methyl cellulose, hydroxypropyl methyl cellulose, and hydroxyethyl cellulose and amorphous silicas, and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol© series. Particularly preferred Carbopols include Carbopol 934, 940, 941, 956, 974P, and mixtures thereof. Silica thickeners such as DT 267 (from PPG Industries) may also be used. One or more thickening agents are optionally present in a total amount of from about 0.01 wt. % to 15 wt. %, for example from about 0.1 wt. % to about 10 wt. %, or from about 0.2 wt. % to about 5 wt. %, by total weight of the composition. Some embodiments comprise sodium carboxymethyl cellulose (e.g., from 0.5 wt. %-1.5 wt. %). In certain embodiments, thickening agents in an amount of about 0.5% to about 5.0% by weight of the total composition are used. Thickeners may be present in an amount of from 1 wt % to 15 wt %, from 3 wt % to 10 wt %, 4 wt % to 9 wt %, from 5 wt % to 8 wt %, for example 5 wt %, 6 wt %, 7 wt %, or 8 wt %.

In some embodiments, the oral care compositions comprise at least one colorant. Colorants herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5% by total weight of the composition.

In some embodiments, the oral care composition further comprises an anti-calculus (tartar control) agent. Suitable anti-calculus agents include, but are not limited to: phosphates and polyphosphates, polyaminopropane sulfonic acid (AM PS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates. Soluble pyrophosphates are useful anticalculus agents. The pyrophosphate salts can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The pyrophosphates also contribute to preservation of the compositions by lowering water activity, tetrasodium pyrophosphate (TSPP), tetrapotassium pyrophosphate, sodium tripolyphosphate, tetrapolyphosphate, sodium trimetaphosphate, sodium hexametaphosphate and mixtures thereof. The salts are useful in both their hydrated and unhydrated forms. An effective amount of pyrophosphate salt useful in the present composition is generally enough to provide least 0.1 wt. % pyrophosphate ions, e.g., 0.1 to 3 wt. %, e.g., 0.1 to 2 wt. %, e.g., 0.1 to 1 wt. %, e.g., 0.2 to 0.5 wt. %.

Other useful tartar control agents include polymers and co-polymers. In some embodiments, the oral care compositions include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water-soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene), having a molecular weight (M.W.) of about 30,000 to about 1,000,000, polyvinyl methyl ether/maleic anhydride (PVM/MA) copolymers such as GANTREZ® (e.g., GANTREZ® S-97 polymer). In some embodiments, the PVM/MA copolymer comprises a copolymer of methyl vinyl ether/maleic anhydride, wherein the anhydride is hydrolyzed following copolymerization to provide the corresponding acid. In some embodiments, PVM/MA copolymer has an average molecular weight (M.W.) of about 30,000 to about 1,000,000, e.g. about 300,000 to about 800,000, e.g., wherein the anionic polymer is about 1-5%, e.g., about 2%, of the weight of the composition. In some embodiments, the anti-calculus agent is present in the composition in an amount of from 0.2 weight % to 0.8 weight %; 0.3 weight % to 0.7 weight %; 0.4 weight % to 0.6 weight %; or about 0.5 weight %, based on the total weight of the composition. Copolymers are available for example as Gantrez AN 139 (M.W. 500,000), AN 1 19 (M.W. 250,000) and S-97 Pharmaceutical Grade (M.W. 70,000), of GAF Chemicals Corporation. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethyl enically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000. Another useful class of polymeric agents includes polyamino acids, particularly those containing proportions of anionic surface-active amino acids such as aspartic acid, glutamic acid and phosphoserine.

In some embodiments, the oral care compositions comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In some embodiments, the oral care compositions comprise a nutrient. Suitable nutrients include vitamins, minerals, amino acids, and mixtures thereof. Vitamins include Vitamins C and D, miamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, the oral care compositions comprise at least one viscosity modifier, useful for example to help inhibit settling or separation of ingredients or to promote re-dispersibility upon agitation of a liquid composition. Any orally acceptable viscosity modifier can be used, including without limitation, mineral oil, petrolatum, clays and organo-modified clays, silicas and the like. One or more viscosity modifiers are optionally present in a total amount of from about 0.01 wt. % to about 10 wt. %, for example, from about 0.1 wt. % to about 5 wt. %, by total weight of the composition.

In some embodiments, the oral care compositions comprise antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt. % to about 20 wt. % by weight based on the total weight of the composition, depending on the agent chosen.

In some embodiments, the oral care compositions comprise an antioxidant. Any orally acceptable antioxidant can be used, including butylated hydroxy anisole (BHA), butylated hydroxytoluene (BHT), vitamin A, carotenoids, co-enzyme Q10, PQQ, Vitamin A, Vitamin C, vitamin E, anethole-dithiothione, flavonoids, polyphenols, ascorbic acid, herbal antioxidants, chlorophyll, melatonin, and mixtures thereof.

In some embodiments, the oral care compositions comprise a source of calcium and phosphate selected from (i) calcium-glass complexes, e.g., calcium sodium phosphosilicates, and (ii) calcium-protein complexes, e.g., casein phosphopeptide-amorphous calcium phosphate. Any of the preceding compositions further comprising a soluble calcium salt, e.g., selected from calcium sulfate, calcium chloride, calcium nitrate, calcium acetate, calcium lactate, and combinations thereof.

In some embodiments, the oral care compositions comprise an additional ingredient selected from: benzyl alcohol, Methylisothizolinone ("MIT"), Sodium bicarbonate, sodium methyl cocoyl taurate (tauranol), lauryl alcohol, and polyphosphate. Some embodiments comprise benzyl alcohol that is present from 0.1-0.8 wt %, or 0.2 to 0.7 wt %, or from 0.3 to 0.6 wt %, or from 0.4 to 0.5 wt %, e.g. about 0.1 wt. %, about 0.2 wt. %, about 0.3 wt %, about 0.4 wt %, about 0.5 wt %, about 0.6 wt %, about 0.7 wt % or about 0.8 wt %.

EXAMPLES

Example 1

Mucin 5B is a secreted glycoprotein in saliva. Its functions include: binding pathogens to prevent infection, enhancing pellicle formation and retention and signal transduction in immune function. Mucin 5B facilitates bulk removal and keeps pathogens dispersed.

Oral mucosa protein sIgA's function is primary immune defense. It reduces bacterial adherence. Immune exclusion by binding foreign antigens and preventing adherence to mucosa resulting in elimination by swallowing/expectoration. SIgA is present in a diurnal rhythm—highest levels in the morning, lowest levels in the evening.

Experiments were performed to determine the impact of an experimental toothpaste that comprises Fluoride (0.454% $SnF_2$) and Zinc Phosphate (1.0% $Zn_3(PO_4)_2$) on sIgA and MUC5B levels in saliva, on cheek cell surfaces, and in cheek cell contents. The clinical study was a 4 week clinical study; a 2 week washout period with a control toothpaste was followed by 2 weeks with experimental toothpaste. 16 human subjects were enrolled. During the 2 week washout period, 2 baseline sample collections were undertaken: one at day 7 and one at day 14. Saliva and cheek cell swabs were collected. During the 2 week testing period, 2 sample collections were undertaken: one at day 21 and one at day 28. Saliva and cheek cell swabs were collected.

The control toothpaste comprised Fluoride (0.76% $Na_2FPO_4$). The test toothpaste comprised Fluoride (0.454% $SnF_2$) and Zinc Phosphate (1.0% $Zn_3(PO_4)_2$). Test subjects brushed their teeth two times per day with assigned toothpaste.

Saliva was collected by having the subject spit saliva into a collection tube. A Buccal cell swab was taken on each cheek and underneath lips with histobrushes.

Saliva samples were tested for sIgA, MUC5B, or total protein by ELISA assay. Cheek cell samples were tested by ELISA assay for Surface MUC5B, Surface Total Protein, Intracellular MUC5B and Intracellular Total Protein. Cheek cell Surface sIgA was also assessed by flow cytometry.

Human MUC5B ELISA kit LS-F4869 (LifeSpan BioSciences, Inc) was used to assay MUC 5B. Salimetrics Salivary Secretory IgA (SIgA, Secretory Immunoglobulin-A) Enzyme Immunoassay Kit (Salimetrics) was used to assay sIgA. Anti-Human IgA-FITC=Anti-Human IgA (a-chain specific)—FITC antibody produced in goat (F5259-2ML, Sigma, 1001859391) was used. Micro BCA (Bicinconinic Acid) Protein Assay ThermoFisher Scientific Cat #23235 was used to assay total protein. Flow Cytometer Analysis was performed using an Attune NxT Flow Cytometer (ThermoFisher Scientific). Flow Cytometry Staining Buffer Solution (eBioscience, 00-4222-26) was used.

Figure 2:
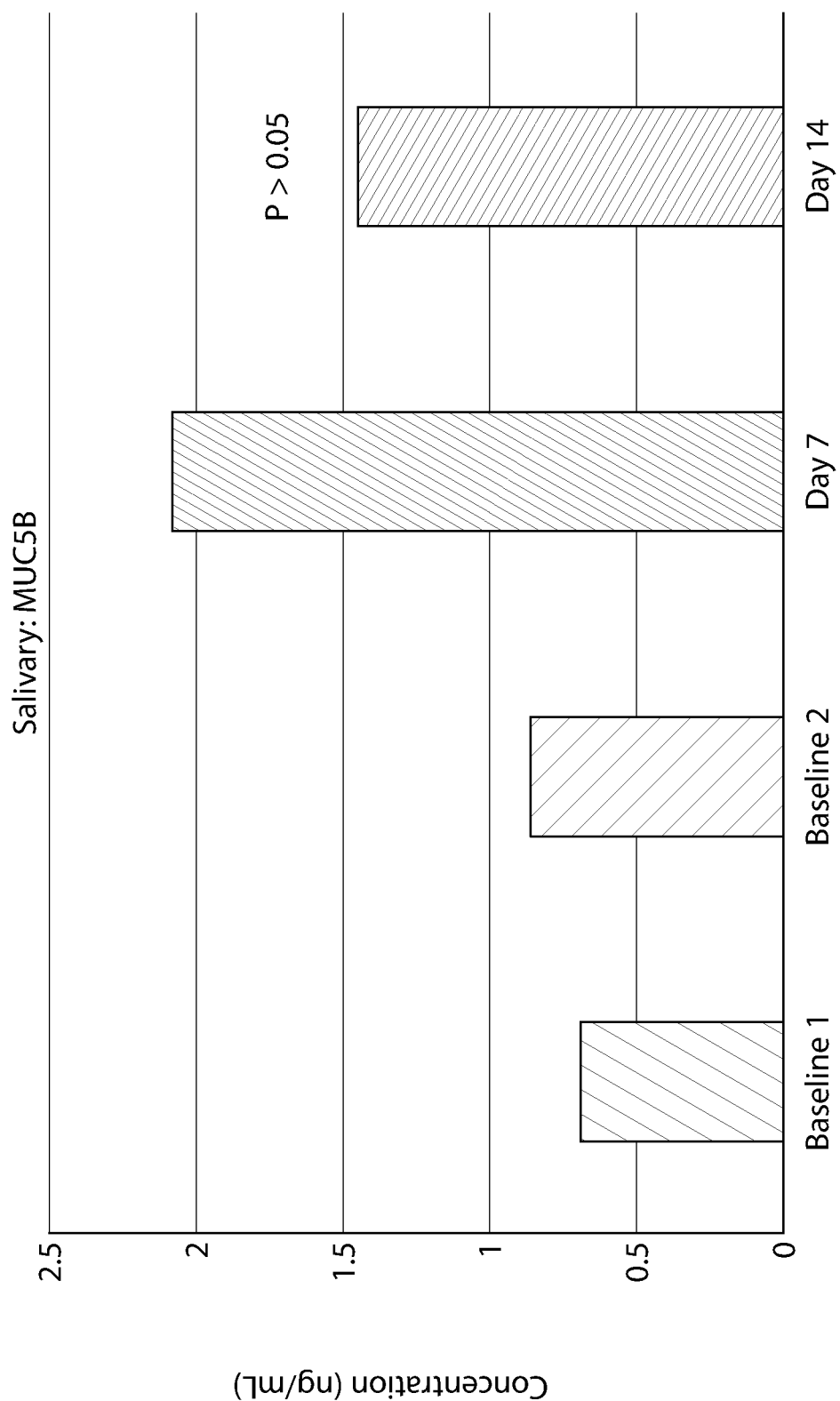
FIG. 2 shows data from ELISA assays of saliva samples tested for MUC5B.
Figure 3:
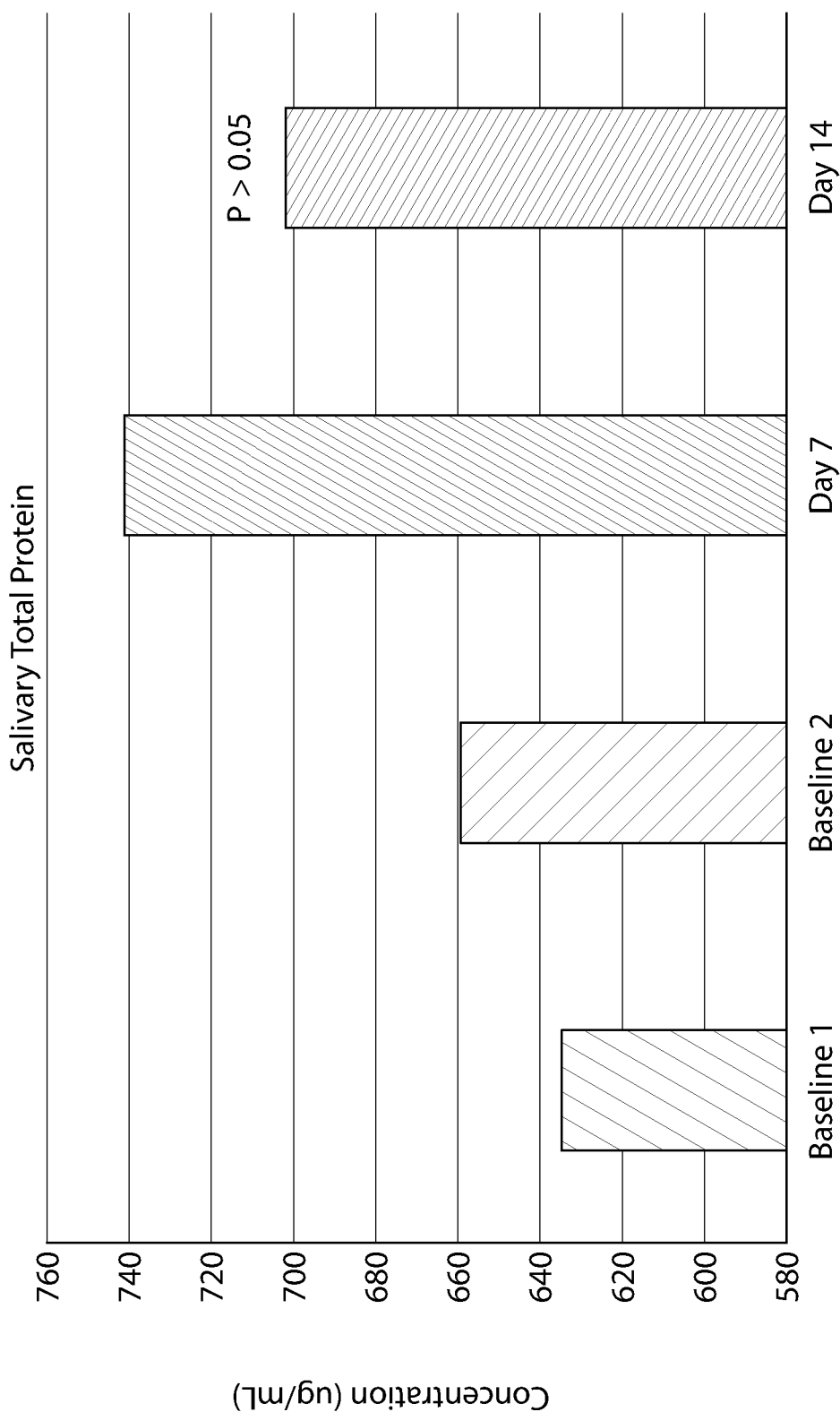
FIG. 3 shows data from ELISA assays of saliva samples tested for total protein.
Figure 4:
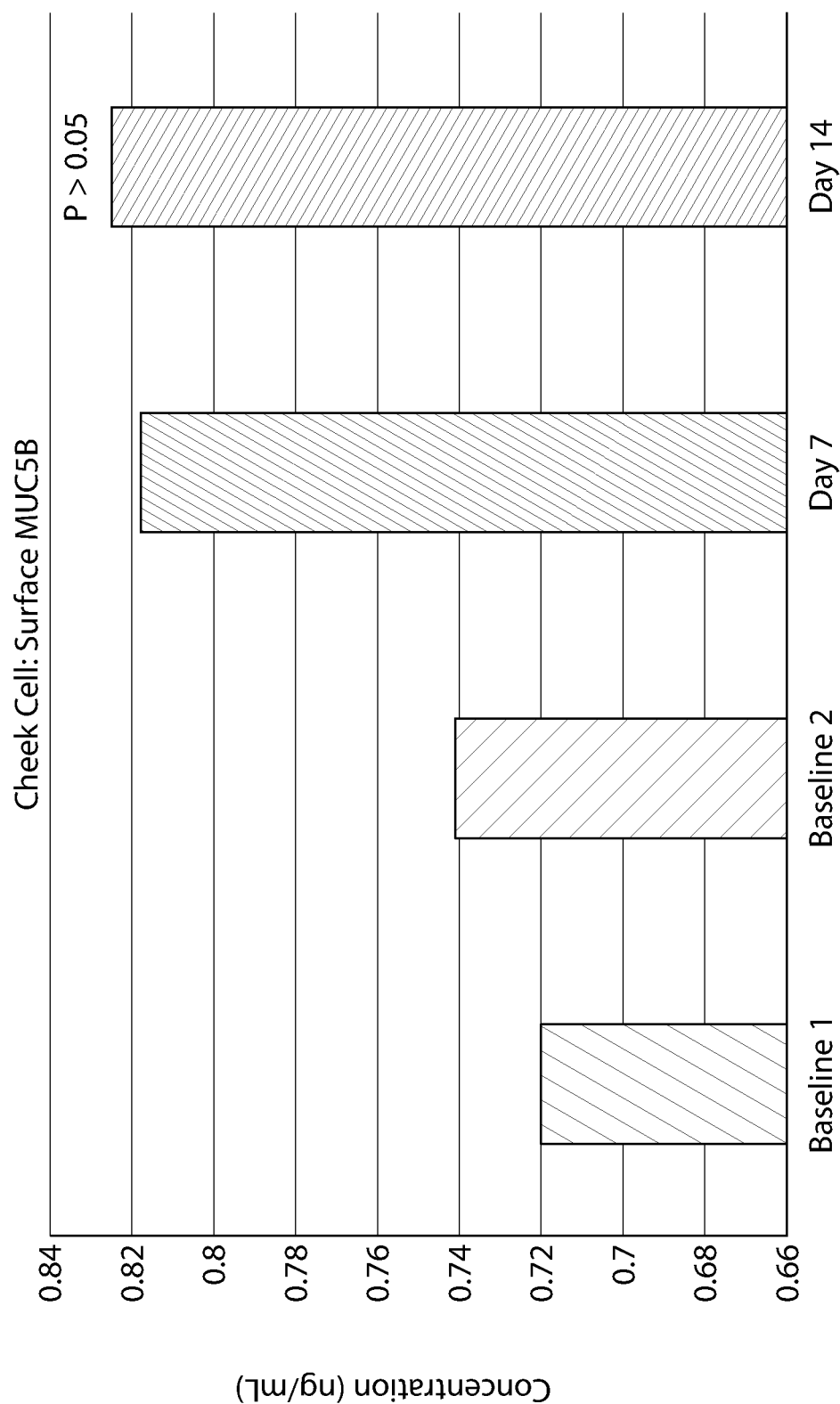
FIG. 4 shows data from ELISA assays of cheek cell samples tested for surface MUC5B.
Figure 5:
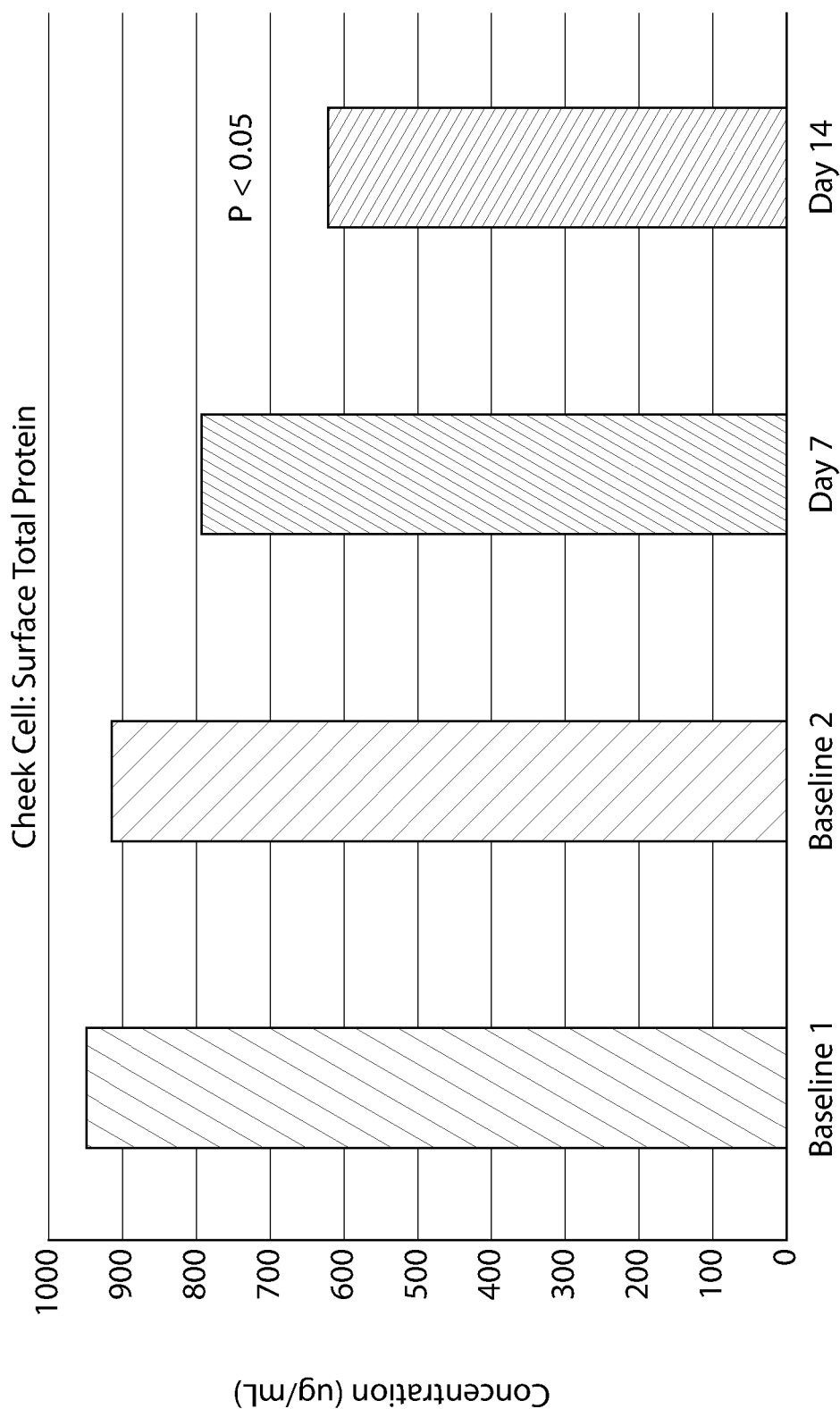
FIG. 5 shows data from ELISA assays of cheek cell samples tested for surface total protein.
Figure 6:
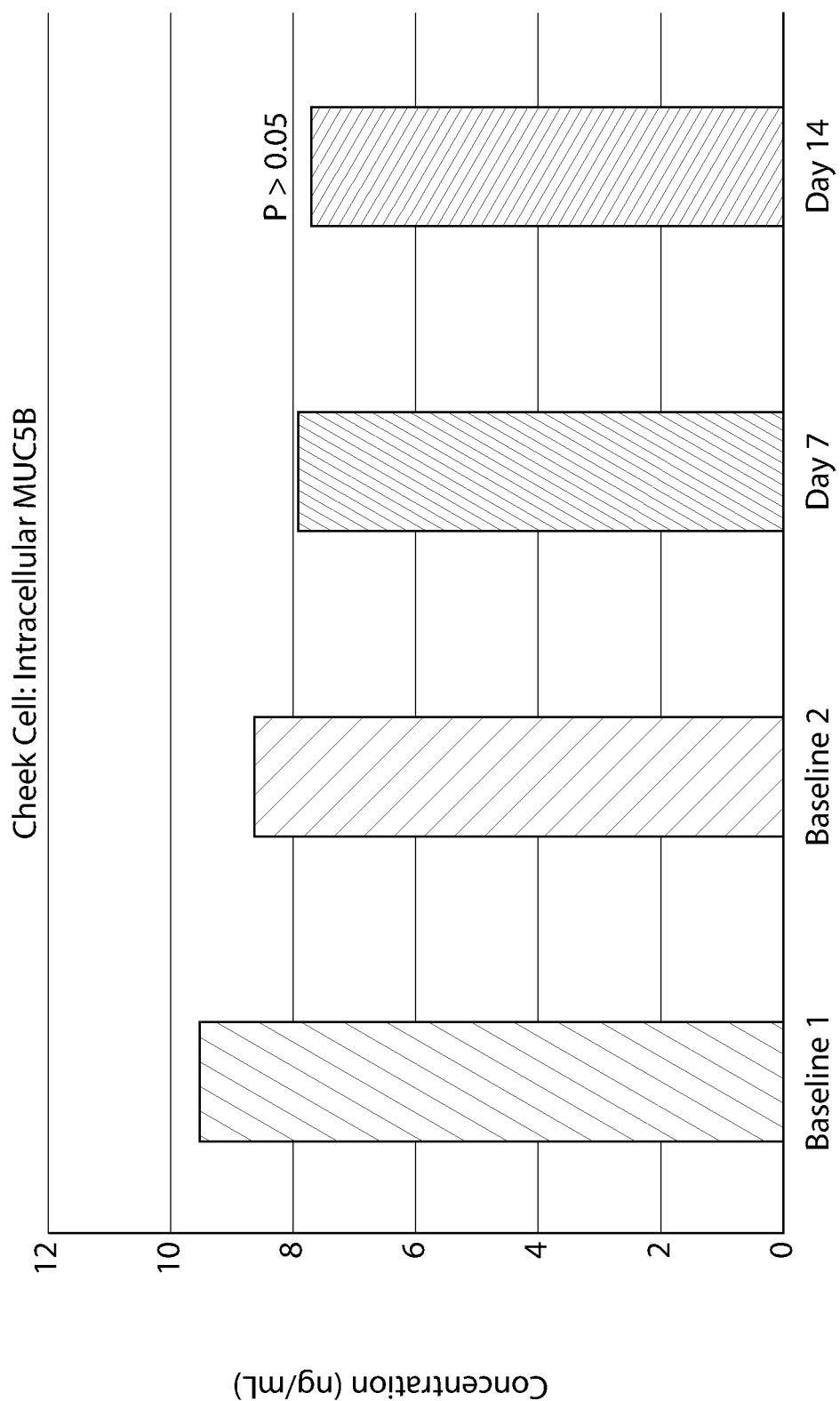
FIG. 6 shows data from ELISA assays of cheek cell samples tested for intracellular MUC5B.
Figure 7:
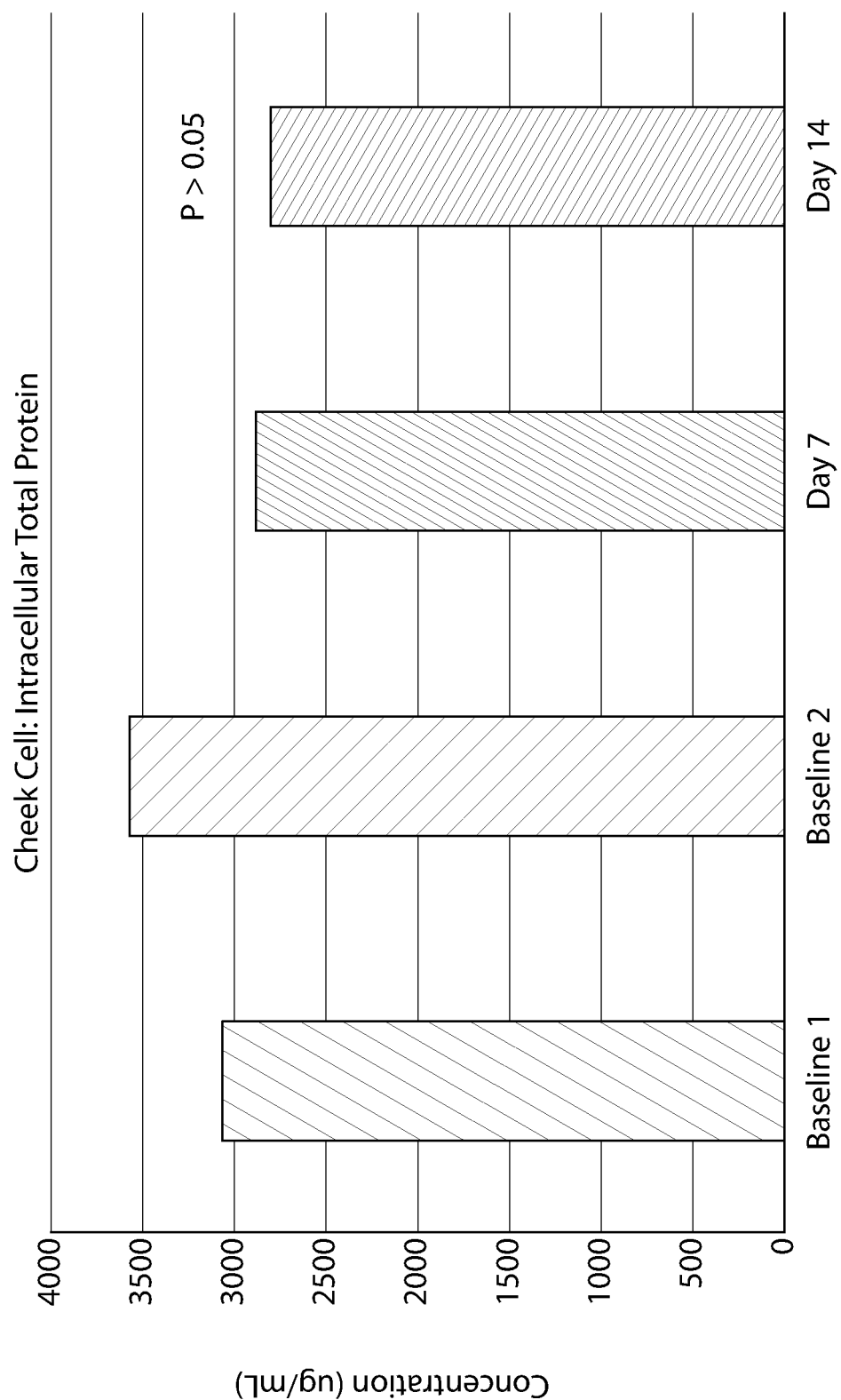
FIG. 7 shows data from ELISA assays of cheek cell samples tested for intracellular total protein.

Table 1 lists the ELISA data. FIGS. 1-3 show data from ELISA assays of saliva samples tested for sIgA, MUC5B, or total protein, respectively. FIGS. 4-7 show data from ELISA assays of Cheek cell samples tested for Surface MUC5B, Surface Total Protein, Intracellular MUC5B and Intracellular Total Protein, respectively. The ELISA assay data showed that salivary sIgA significantly increased after treatment with experimental toothpaste (FIG. 1). Data from ELISA assays showed that both salivary Mucin5B (FIG. 2) and surface Mucin5B (FIG. 4) increased after treatment with experimental toothpaste. Salivary total protein (FIG. 3) also increased after treatment with experimental toothpaste while surface total protein (FIG. 5) significantly decreased after treatment with experimental toothpaste. Cheek cell intracellular Mucin5B (FIG. 6) and cheek cell intracellular total protein (FIG. 7) both decreased after treatment.

TABLE 1

| ELISA data | | | | | |
| --- | --- | --- | --- | --- | --- |
|  | Figure | Baseline 1 | Baseline 2 | Day 7 | Day 14 |
| Salivary sIgA | 1 | 180.519 | 147.995 | 160.373 | 256.314 |
| Salivary MUC5B | 2 | 0.689 | 0.862 | 2.0785 | 1.449 |
| Salivary Total Protein | 3 | 634.109 | 658.836 | 741.280 | 701.621 |
| Cheek Cell: Surface MUC5B | 4 | 0.720 | 0.741 | 0.818 | 0.825 |
| Cheek Cell: Surface Total Protein | 5 | 950.629 | 919.664 | 793.742 | 624.278 |
| Cheek Cell: Intracellular MUC5B | 6 | 9.548 | 8.636 | 7.916 | 7.721 |
| Cheek Cell: Intracellular Total Protein | 7 | 3077.155 | 3573.189 | 2886.669 | 2804.026 |

Figure 8:
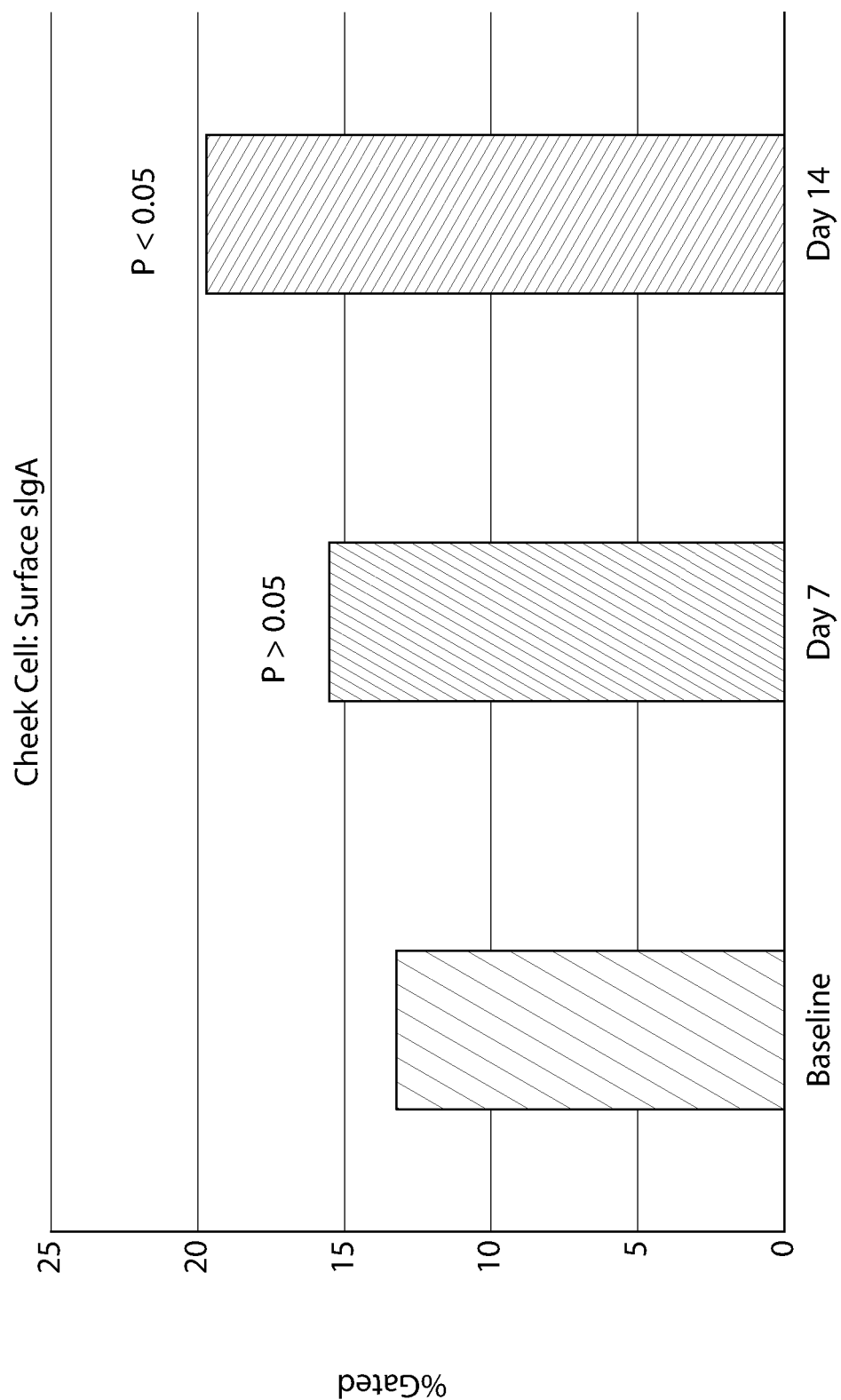
FIG. 8 shows flow cytometry data for cheek cell surface sIgA: % gated.
Figure 9:
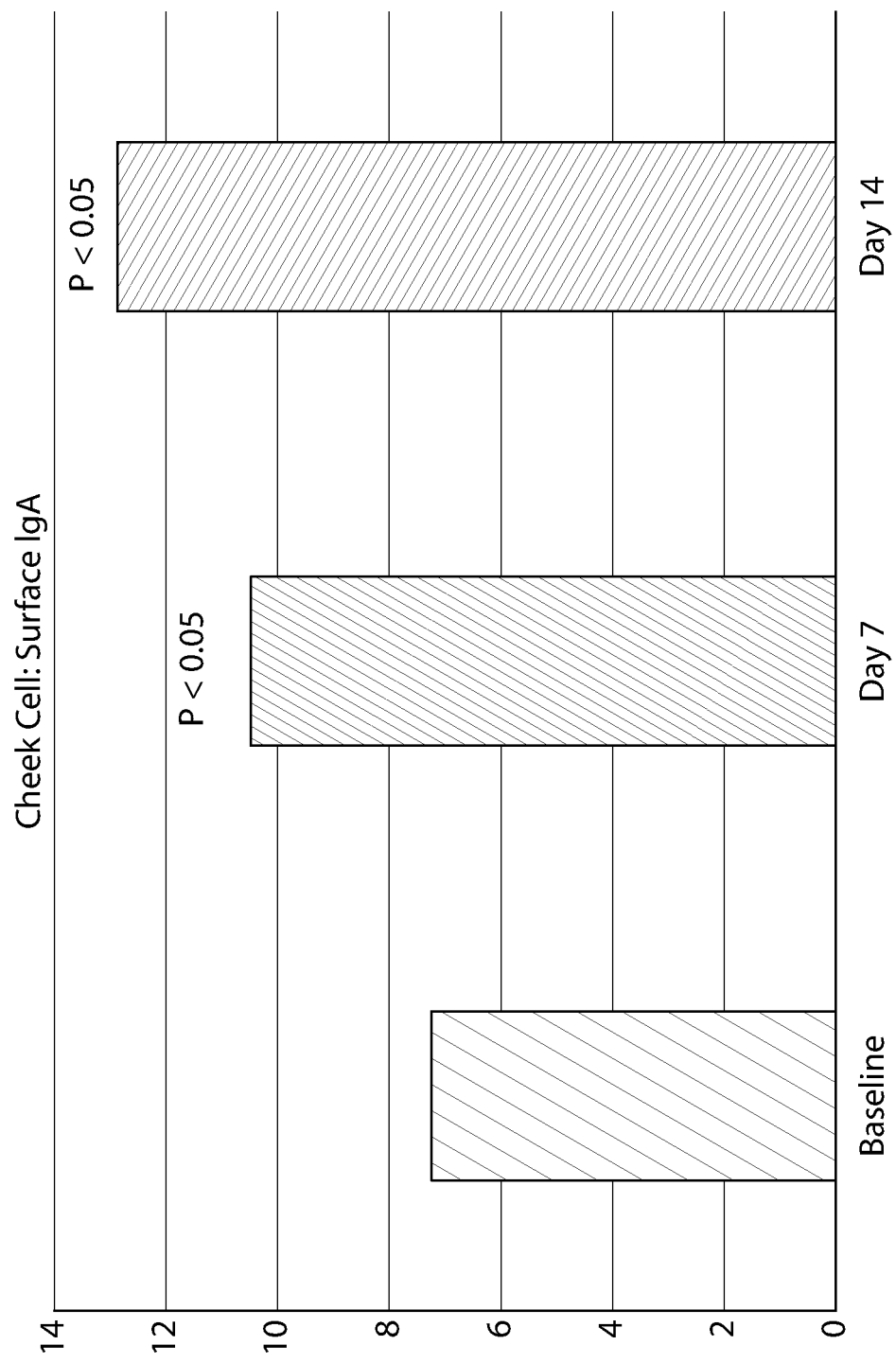
FIG. 9 shows flow cytometry data for cheek cell surface sIgA: % total.

The data from flow cytometry is shown in FIGS. 8 and 9. FIG. 8 shows flow cytometry data for cheek cell surface sIgA: % gated. FIG. 9 shows flow cytometry data for cheek cell surface sIgA: % total. FIG. 8 showed that Surface sIgA significantly increases 14 days after treatment. FIG. 9 showed that Surface sIgA significantly increases 7 days and continues to increase after treatment.

In summary, the experimental toothpaste significantly increased sIgA levels on buccal cell surfaces and in saliva. Elevated levels of sIgA indicates better immune defense against bacteria in the mouth. Elevated Mucin 5B indicates aggregating more bacteria and better lubrication. SnF2 with Zinc allows for the removal of more bacteria from the mouth and higher immune defense system on the mucosal surface.

Example 2

Oral compositions that comprise arginine are disclosed in WO 2017/223292, which is incorporated herein by reference. In some embodiments, the oral care composition comprises an orally acceptable carrier, zinc phosphate; and stannous fluoride. In some embodiments, the zinc phosphate is a preformed salt of zinc phosphate. In some embodiments, the zinc phosphate is present in an amount sufficient so that the stannous fluoride dissociates to provide a therapeutically effective amount of stannous ions in aqueous solution. In some embodiments, the amount of zinc phosphate is from 0.05 to 5% by weight, relative to the weight of the oral care composition. In some embodiments, the amount of the stannous fluoride is from 0.05% to 5% by weight relative to the weight of the oral care composition. In some embodiments, the amount of the water is about 12% by weight or more, relative to the weight of the oral care composition. In some embodiments, the oral care composition further comprises an abrasive and/or one or more humectants and/or one or more surfactants. In some embodiments, the oral care composition further comprises an effective amount of one or more alkali phosphate salts and/or a whitening agent. In some embodiments, the oral care composition further comprising one or more sources of zinc ions in addition to the zinc phosphate. In some embodiments, the oral care composition is a dentifrice, powder, cream, strip, gum or gel. In some embodiments, the oral care composition comprises: from 0.5 to 3% by weight zinc phosphate; from 0.05 to 11% by weight stannous fluoride; from 1 to 8% by weight alkali phosphate salts selected from sodium phosphate dibasic, potassium phosphate dibasic, dicalcium phosphate dihydrate, tetrasodium pyrophosphate, tetrapotassium pyrophosphate, calcium pyrophosphate, sodium tripolyphosphate, and mixtures of any two or more of these, relative to the weight of the oral care composition; and a silica abrasive. In some embodiments, the oral care composition has a pH that is less than 7.

Example 3

Oral compositions that comprise arginine are disclosed in WO 2017/223311, which is incorporated herein by reference. The oral care composition is an oral care composition set out in Example 4 that further comprises an organic acid buffer system. In some embodiments, the oral care composition comprises an amount of the water that is 10% by weight or more, relative to the weight of the oral care composition. In some embodiments, the organic buffer system comprises a carboxylic acid and one or more conjugate base salts thereof, for example, alkali metal salts thereof. In some embodiments, the acid is selected from citric acid, lactic acid, malic acid, maleic acid, fumaric acid, acetic acid, succinic acid, and tartaric acid. In some embodiments, the one or more conjugate base salts are independently selected from sodium and potassium salts, or combinations thereof. In some embodiments, the acid is citric acid, and the one or more conjugate base salts comprise monosodium citrate (monobasic), di sodium citrate (dibasic), trisodium citrate (tribasic), and combinations thereof. In some embodiments, the oral care compositions comprise the organic acid buffer system in an amount of 0.1 to 5.0% by weight of the composition, measured as the combined amount of organic acid and any conjugate base salt. In some embodiments, the buffer system comprises citric acid and a sodium citrate salt, in a ratio of from 1:3 to 1:6.

Example 4

Test dentifrices comprising zinc phosphate and stannous fluoride were prepared as shown in Formulation Tables A-D

| Formulation Table A | |
|---|---|
| Ingredient | |
| Water | QS (e.g. 15-40) |
| Thickener | 0.5-5 (e.g. 3.6) |
| Humectants | 15-55 (e.g. 48) |
| Tarter control agents | 0.5-5 (e.g. 2) |
| Abrasives | 10-30 (e.g. 20) |
| Stannous Fluoride | 0.5-11 (e.g. 0.454) |
| Minors (flavor, color) | 0.5-5 (e.g. 2.25) |
| Surfactants | 0.1-15 (e.g. 2.75) |
| Zinc phosphate | 0.5-5 (e.g. 1 or 2) |

| Formulation Table B | |
|---|---|
| Ingredient | |
| Water and Minors (flavor, color) | 11.74 |
| Stannous Fluoride | 0.454 |
| Zinc phosphate | 1.15 |
| Thickener | 2.9 |
| Glycerin | 40.79 |
| Abrasive Silica | 24.00 |
| Propylene glycol | 4.00 |
| Trisodium citrate trihydrate | 3.00 |
| Sodium tripolyphosphate | 3.00 |
| Polyethylene glycol 600 | 3.00 |
| Tetrasodium pyrophosphate | 2.00 |
| Anionic Surfactant | 1.75 |
| Zwitterionic Surfactant | 1.0 |
| Anionic polymer | 0.61 |
| Citric acid | 0.60 |

| Formulation Table C | |
|---|---|
| Ingredient | |
| Zinc phosphate | 0.5-2.5 (e.g. about 1) |
| Stannous Fluoride | 0.3-1 (e.g. about 0.45) |
| Alkali metal pyrophosphate (Tetrapotassium pyrophosphate, Tetrasodium pyrophosphate) | 1-5 (e.g. about 2 or 4) |
| Sodium citrate (Trisodium citrate dihydrate) | 0.8-2.5 (e.g. about 1) |
| Citric Acid | 0.15-0.5 (e.g. about 0.2) |
| Anionic Surfactant (sodium lauryl sulfate) | 1-3 (e.g. about 1.5) |
| Zwitterionic Surfactant (CAPB) | 1-3 (e.g. about 1.25) |
| Sorbitol (e.g. 70% sorbitol) | 20-50 (e.g. about 40) |
| Glycerin | 1-8 (e.g. about 4) |
| Gum polymer (xanthan gum) | 0.5-2 (e.g. about 0.3) |
| Polyethylene glycol (PEG 600) | 1-5 (e.g. about 2) |
| Carboxymethyl cellulose (NaCMC) | 0.5-3 (e.g. about 2) |
| Water (added water) | 10-30, 15-20 (e.g. about 20) |
| Water) | 20-50 (e.g. about 30) |

| Formulation Table D | | |
|---|---|---|
| Ingredient | | |
| Water | QS (e.g. 15-40) | QS (e.g. 15-25) |
| Humectants | 15-55 (e.g. 40) | 40 |
| Abrasives | 10-30 (e.g. 20) | 20 |
| Thickeners | 0.5-5 (e.g. 3.6) | 3.6 |
| Organic acid buffer salt (Trisodium citrate) | 0.0-0.6 | 0.0-0.6 |
| Zinc phosphate | 0.5-5 (e.g. 2.3) | 2.3 |
| Flavors, sweeteners, colors | 0.5-5 (e.g. 0.65) | 0.65 |
| Alkali phosphate salts | 0.5-5 (e.g. 2) | 2 |
| Anionic Surfactant | 0.01-10 (e.g. 1.5) | 1.5 |
| Zwitterionic Surfactant | 0.01-4.5 (e.g. 1.25) | 1.25 |
| Organic acid buffer acid | 0.0-0.3 | 0.0-0.3 |
| Stannous Fluoride | 0.5-11 (e.g. 0.454) | 0.454 |

The invention claimed is:

1. A method of increasing sIgA and mucin 5B levels in an individual's oral cavity, the method comprising
applying to the individual's oral cavity twice daily for 14 consecutive days in an amount effective to increase sIgA and mucin 5B levels in the individual's oral cavity, an oral care composition comprising: zinc phosphate, stannous fluoride and optionally, an organic acid buffer system; wherein the sIgA level in saliva is increased to above 250 ug/mL, the level of MUC 5B in saliva is increased to 1.449 ng/mL and the level of MUC 5B on cheek cell surface is increased to above 0.8 ng/mL.

2. The method of claim 1, wherein the oral care composition is a toothpaste.

3. The method of claim 1, wherein the zinc phosphate is a preformed salt of zinc phosphate.

4. The method of claim 1, wherein zinc phosphate is present in an amount sufficient so that the stannous fluoride dissociates to provide a therapeutically effective amount of stannous ions in aqueous solution.

5. The method of claim 1, wherein the amount of zinc phosphate is from 0.05 to 5% by weight, relative to the weight of the oral care composition.

6. The method of claim 1, wherein the amount of the stannous fluoride is from 0.05% to 5% by weight relative to the weight of the oral care composition.

7. The method of claim 1, wherein the oral care composition further comprises water and the amount of the water is about 10% by weight or more, relative to the weight of the oral care composition.

8. The method of claim 1, wherein the oral care composition further comprises water and the amount of the water is about 12% by weight or more, relative to the weight of the oral care composition.

9. The method of claim 1, wherein the organic buffer system comprises a carboxylic acid and one or more conjugate base salts thereof, for example, alkali metal salts thereof.

10. The method of claim 9, wherein the acid is selected from citric acid, lactic acid, malic acid, maleic acid, fumaric acid, acetic acid, succinic acid, and tartaric acid.

11. The method of claim 9, wherein the one or more conjugate base salts are independently selected from sodium and potassium salts, or combinations thereof.

12. The method of claim 9, wherein the acid is citric acid, and the one or more conjugate base salts comprise monosodium citrate (monobasic), disodium citrate (dibasic), trisodium citrate (tribasic), and combinations thereof.

13. The method of claim 1, wherein the oral care composition comprises the organic acid buffer system in an amount of 0.1 to 5.0% by weight of the composition, measured as the combined amount of organic acid and any conjugate base salt.

14. The method of claim 1, wherein the buffer system comprises citric acid and a sodium citrate salt, in a ratio of from 1:3 to 1:6.

15. The method of claim 1, wherein the oral care composition further comprises an abrasive.

16. The method of claim 1, wherein the oral care composition further comprises one or more humectants.

17. The method of claim 1, wherein the oral care composition further comprises one or more surfactants.

18. The method of claim 1, wherein the oral care composition further comprises an effective amount of one or more alkali phosphate salts.

19. The method of claim 1, wherein the oral care composition further comprises a whitening agent.

20. The method of claim 1, wherein the oral care composition further comprises one or more sources of zinc ions in addition to the zinc phosphate.

21. The method of claim 1, wherein the oral care composition is a dentifrice, powder, cream, strip, gum or gel.

22. The method of claim 1, wherein the oral care composition comprises:
from 0.5 to 3% by weight zinc phosphate;
from 0.05 to 11% by weight stannous fluoride;
from 1 to 8% by weight alkali phosphate salts selected from sodium phosphate dibasic, potassium phosphate dibasic, dicalcium phosphate dihydrate, tetrasodium pyrophosphate, tetrapotassium pyrophosphate, calcium pyrophosphate, sodium tripolyphosphate, and mixtures of any two or more of these, relative to the weight of the oral care composition; and
a silica abrasive.

23. The method of claim 1, wherein the pH of the oral care composition is less than 7.

24. The method of claim 1, wherein the sIgA and mucin 5B levels are measured the day prior to the 14 consecutive days and on day 14 of the 14 consecutive days and the sIgA levels in an individual's oral cavity that are increased are salivary sIgA levels in the individual's oral cavity, the method comprising the steps of:
determining baseline levels of sIgA and mucin 5B in the individual's oral cavity by obtaining baseline samples of saliva, cheek cell surfaces and cheek cells from the individual and measuring sIgA and mucin 5B levels in the baseline samples;
after obtaining the baseline samples, applying the oral care composition to the individual's oral cavity twice daily for 14 consecutive days; and
on day 14 of the 14 consecutive days of applying the oral care composition to the individual's oral cavity twice daily, determining levels of sIgA and mucin 5B in the individual's oral cavity by obtaining samples of saliva, cheek cell surfaces and cheek cells from the individual and measuring sIgA and mucin 5B levels in the samples.

25. The method of claim 1, wherein the sIgA level in saliva is increased to 256.314 ug/mL, the level of MUC 5B in saliva is increased to 1.449 ng/mL and the level of MUC 5B on cheek cell surface is increased to 0.825 ng/mL.

26. A method of increasing sIgA and mucin 5B levels in an individual's oral cavity, wherein the sIgA levels in an individual's oral cavity that are increased are salivary sIgA levels in the individual's oral cavity and sIgA and mucin 5B levels are measured the day prior to the 14 consecutive days and on day 14 of the 14 consecutive days, the method comprising the steps of:
- determining baseline levels of sIgA and mucin 5B in the individual's oral cavity by obtaining baseline samples of saliva, cheek cell surfaces and cheek cells from the individual and measuring sIgA and mucin 5B levels in the baseline samples;
- after obtaining the baseline samples, applying to the individual's oral cavity twice daily for 14 consecutive days in an amount effective to increase sIgA and mucin 5B levels in the individual's oral cavity, an oral care composition comprising: zinc phosphate, stannous fluoride and optionally, an organic acid buffer system; and
- on day 14 of the 14 consecutive days of applying the oral care composition to the individual's oral cavity twice daily, determining levels of sIgA and mucin 5B in the individual's oral cavity by obtaining samples of saliva, cheek cell surfaces and cheek cells from the individual and measuring sIgA and mucin 5B levels in the samples.

\* \* \* \* \*